United States Patent
Iwakubo et al.

(10) Patent No.: US 10,336,939 B2
(45) Date of Patent: Jul. 2, 2019

(54) STABILIZER COMPOUND, LIQUID CRYSTAL COMPOSITION, AND DISPLAY DEVICE

(71) Applicant: DIC Corporation, Tokyo (JP)

(72) Inventors: Masayuki Iwakubo, Kita-adachi-gun (JP); Sayaka Nose, Kita-adachi-gun (JP); Manabu Takachi, Kita-adachi-gun (JP); Yoshio Aoki, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/580,090

(22) PCT Filed: Jun. 23, 2016

(86) PCT No.: PCT/JP2016/068664
§ 371 (c)(1),
(2) Date: Dec. 6, 2017

(87) PCT Pub. No.: WO2017/002702
PCT Pub. Date: Jan. 5, 2017

(65) Prior Publication Data
US 2018/0223188 A1 Aug. 9, 2018

(30) Foreign Application Priority Data
Jul. 1, 2015 (JP) .................. 2015-132699

(51) Int. Cl.
*C07D 401/14* (2006.01)
*C09K 19/54* (2006.01)
*C07D 211/48* (2006.01)
*G02F 1/13* (2006.01)
*C07D 211/46* (2006.01)
*C09K 19/34* (2006.01)

(52) U.S. Cl.
CPC ............ *C09K 19/54* (2013.01); *C07D 211/46* (2013.01); *C07D 211/48* (2013.01); *C09K 19/3444* (2013.01); *G02F 1/13* (2013.01)

(58) Field of Classification Search
CPC .......... C07D 401/14; C09K 2019/0414; C08K 5/3435
USPC ....................... 546/188; 252/299.61
See application file for complete search history.

(56) References Cited

U.S. PATENT DOCUMENTS

| | | |
|---|---|---|
| 4,075,165 A | 2/1978 | Soma et al. |
| 4,124,564 A | 11/1978 | Minagawa et al. |
| 4,141,883 A | 2/1979 | Soma et al. |
| 4,238,613 A | 12/1980 | Rasberger et al. |
| 4,396,735 A | 8/1983 | Minagawa et al. |
| 4,404,301 A | 9/1983 | Kubota et al. |
| 4,668,722 A | 5/1987 | Mack |
| 4,906,604 A | 3/1990 | Okamoto et al. |
| 5,439,958 A | 8/1995 | Scrima et al. |
| 2004/0157064 A1 | 8/2004 | Aoki |
| 2006/0189777 A1 | 8/2006 | Aoki |
| 2008/0003439 A1 | 1/2008 | Aoki |
| 2008/0231788 A1 | 9/2008 | Yoshida et al. |
| 2009/0142515 A1 | 6/2009 | Nakamura et al. |
| 2010/0149950 A1 | 6/2010 | Yoshida et al. |
| 2011/0037910 A1 | 2/2011 | Yoshida et al. |
| 2012/0268706 A1 | 10/2012 | Goebel et al. |
| 2015/0159088 A1 | 6/2015 | Goebel et al. |
| 2015/0192852 A1 | 7/2015 | Sato et al. |
| 2015/0337202 A1 | 11/2015 | Furusato et al. |
| 2016/0039758 A1 | 2/2016 | Gotoh et al. |
| 2016/0090534 A1 | 3/2016 | Gotoh et al. |
| 2017/0158960 A1 | 6/2017 | Sudo et al. |

FOREIGN PATENT DOCUMENTS

| | | |
|---|---|---|
| EP | 0 518 807 A1 | 12/1992 |
| EP | 0 636 610 A1 | 2/1995 |
| EP | 2 982 731 A1 | 2/2016 |
| JP | 51-132242 A | 11/1976 |
| JP | 51-139841 A | 12/1976 |
| JP | 52-100543 A | 8/1977 |
| JP | 54-72248 A | 6/1979 |
| JP | 57-177053 A | 10/1982 |
| JP | 2001-114762 A | 4/2001 |
| JP | 2004-190013 A | 7/2004 |
| JP | 2006-37054 A | 2/2006 |
| WO | 2007/046384 A1 | 4/2007 |
| WO | 2007/072643 A1 | 6/2007 |
| WO | 2014/045783 A1 | 3/2014 |
| WO | 2016/006524 A1 | 1/2016 |

OTHER PUBLICATIONS

Zeika et al ., "Synthesis of Polynitroxides Based on Nucleophilic Aromatic Substitution", Organic Letters, 2010, vol. 12, No. 16, pp. 3696-3699, Cited in ISR (4 pages).

(Continued)

*Primary Examiner* — Charanjit Aulakh
(74) *Attorney, Agent, or Firm* — Westerman, Hattori, Daniels & Adrian, LLP

(57) ABSTRACT

Provided are a compound represented by general formula (I), a liquid crystal composition that uses the compound, and a liquid crystal display device that uses the liquid crystal composition. Adding the compound represented by general formula (I) to a liquid crystal composition can prevent degradation of the liquid crystal composition by light, heat, etc. The compound represented by general formula (I) dissolves well in the liquid crystal composition. Thus, when the compound represented by general formula (I) is used, a liquid crystal composition having both low viscosity ($\eta$) and high reliability can be prepared, and a high-speed response liquid crystal display device can be provided.

6 Claims, No Drawings

(56) References Cited

OTHER PUBLICATIONS

Luckhurst et al., "Electron Paramagnetic Resonance of Quartet Ground State in Luquid Cristal Solutions", Izvestiya Akademii Nauk SSSR, Seriya Khimicheskaya, 1968, vol. 8, pp. 1708-1710, Cited in ISR, w/English translation (6 pages).
International Search Report dated Aug. 9, 2016, issued in counterpart International Application No. PCT/JP2016/068664 (5 pages).

STABILIZER COMPOUND, LIQUID CRYSTAL COMPOSITION, AND DISPLAY DEVICE

TECHNICAL FIELD

The present invention relates to a stabilizer compound useful for various materials, such as resins and materials for liquid crystal display devices.

BACKGROUND ART

Liquid crystal display devices are mainly used in monitors of televisions and personal computers, and mobile appliances such as smart phones. Examples of the liquid crystal display mode include twisted nematic (TN) mode, super twisted nematic (STN) mode, and vertical alignment (VA) mode, in-plane-switching (IPS) mode, and fringe field switching (FFS) mode that use thin film transistors (TFTs). There are three main properties desired for the liquid crystal display devices: (1) high-speed response, (2) low drive voltage, and (3) a wide operation temperature range with room temperature at the center. Another is (4) high reliability in an operation environment under light or heat.

Roughly speaking, a liquid crystal composition is required to have the following properties in order to satisfy the respective properties (1) to (3) above: (a) low viscosity ($\eta$), (b) a large absolute value of dielectric anisotropy ($\Delta\epsilon$), and (c) a high nematic phase-isotropic liquid phase transition temperature ($T_{ni}$) (PTL 1). Furthermore, the refractive index anisotropy ($\Delta n$) must be adjusted to be within an appropriate range for the cell gap. In order to satisfy the property (4) described above (in order to enhance reliability of the liquid crystal display device), the liquid crystal composition is also required to be stable against external stimuli such as light, heat, moisture, and air (d).

CITATION LIST

Patent Literature

PTL 1 Japanese Unexamined Patent Application Publication No. 2006-37054

SUMMARY OF INVENTION

Technical Problem

An object to be achieved by the invention of the present application is to provide a stabilizer compound that prevents degradation of a liquid crystal composition and has high solubility in the liquid crystal composition.

Solution to Problem

The inventors of the present application have conducted extensive studies to achieve the object described above and made the invention of the present application. In other words, the present invention provides a compound represented by general formula (I):

[Chem. 1]

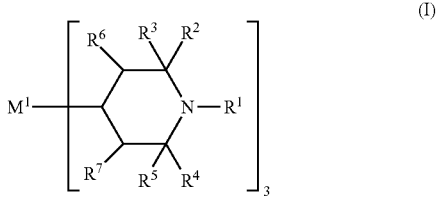

(In the formula, $R^1$ represents a hydrogen atom, —O—, —OH, or an alkyl group having 1 to 12 carbon atoms, and one or two or more —$CH_2$— present in the alkyl group may each independently be substituted with —O—, —S—, —CH=CH—, —C≡C—, —CO—, —CO—O—, —O—CO—, —$OCF_2$—, or —$CF_2O$—, $R^2$, $R^3$, $R^4$, and $R^5$ each independently represent an alkyl group having 1 to 8 carbon atoms, one or two or more —$CH_2$— present in the alkyl group may each independently be substituted with —O—, —S—, —CH=CH—, —C≡C—, —CO—, —CO—O—, —O—CO—, —$OCF_2$—, or —$CF_2O$—, and $R^2$ and $R^3$ and/or $R^1$ and $R^5$ may be bonded with each other to form a ring, $R^6$ and $R^7$ each independently represent a hydrogen atom or an alkyl group having 1 to 6 carbon atoms, and one or two or more —$CH_2$— present in the alkyl group may each independently be substituted with —O—, —S—, —CH=CH—, —C≡C—, —CO—, —CO—O—, —O—CO—, —$OCF_2$—, or —$CF_2O$—, and $M^1$ represents a trivalent organic group, and $R^1$, $R^2$, $R^3$, $R^4$, $R^5$, $R^6$, and $R^7$ that are each present in a plurality may be the same or different from one another.)

The present invention also provides a liquid crystal composition that contains the compound, and a display device.

Advantageous Effects of Invention

When added to a liquid crystal composition, a stabilizer compound according to the present invention prevents degradation of the liquid crystal composition by light, heat, etc. Moreover, the compound according to the present invention dissolves well in the liquid crystal composition. A liquid crystal composition that has both low viscosity (n) and high reliability can be prepared by using the stabilizer compound according to the present invention, and a high-speed-response liquid crystal display device can be provided.

DESCRIPTION OF EMBODIMENTS

In general formula (I), in order to enhance the ability of stabilizing the liquid crystal composition against light, $R^1$ preferably represents a hydrogen atom, —O—, or —OH, more preferably represents a hydrogen atom or —O—, and yet more preferably represents a hydrogen atom. In order to enhance the solubility in the liquid crystal composition, $R^1$ preferably represents an unsubstituted alkyl group having 1 to 12 carbon atoms, an alkoxy group having 1 to 12 carbon atoms, or an alkenyl group having 3 to 12 carbon atoms, preferably represents an unsubstituted alkyl group having 1 to 8 carbon atoms, an alkoxy group having 1 to 8 carbon atoms, or an alkenyl group having 3 to 8 carbon atoms, and yet more preferably represents an unsubstituted alkyl group having 1 to 4 carbon atoms, an alkoxy group having 1 to 4 carbon atoms, or an alkenyl group having 3 or 4 carbon atoms. Moreover, $R^1$ is preferably linear.

$R^2$, $R^3$, $R^4$, and $R^5$ preferably each independently represent an alkyl group having 1 to 4 carbon atoms, preferably each independently represent an unsubstituted alkyl group, and are preferably linear. More preferably, at least one of $R^2$, $R^3$, $R^4$, and $R^5$ represents a methyl group, and, particularly preferably, $R^2$, $R^3$, $R^4$, and $R^5$ all represent a methyl group. $R^2$ and $R^3$ and/or $R^4$ and $R^5$ may bond with each other to form a ring structure.

$R^6$ and $R^7$ preferably each represent a hydrogen atom or an alkyl group having 1 to 4 carbon atoms, and particularly preferably each represent a hydrogen atom from the viewpoint of ease of production.

$M^1$ may be any trivalent organic group but preferably has a structure represented by general formula (I-M):

[Chem. 2]

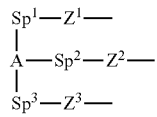

(I-M)

(In the formula, $Z^1$, $Z^2$, and $Z^3$ each independently represent —O—, —S—, —CH=CH—, —C≡C—, —CO—, —CO—O—, —O—CO—, —OCF$_2$—, —CF$_2$O—, —NH—, or a single bond, Sp$^1$, Sp$^2$, and Sp$^3$ each independently represent a single bond or an alkylene group having 1 to 10 carbon atoms, and one or two or more —CH$_2$— present in the alkylene group may be each independently substituted with —O—, —S—, —CH=CH—, —C≡C—, —CO—, —CO—O—, —O—CO—, —OCF$_2$—, or —CF$_2$O—, and A represents a group selected from

[Chem. 3]

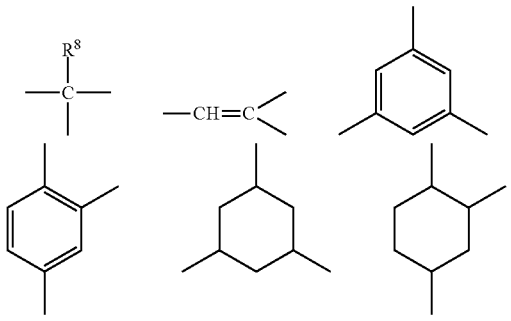

(In the formula, $R^8$ represents a hydrogen atom, —OH, or an alkyl group having 1 to 10 carbon atoms, and one or two or more —CH$_2$— present in the alkyl group may each independently be substituted with —O—, —S—, —CH=CH—, —C≡C—, —CO—O—, or —O—CO—, and a hydrogen atom in the ring structure may be substituted with a halogen atom or a cyano group)) in order to enhance the solubility in the liquid crystal composition and storage stability.

Here, from the viewpoints of ease of production and ready availability of the raw materials, at least one of $Z^1$, $Z^2$, and $Z^3$ preferably represents —O—, —CO—O—, or a single bond and particularly preferably $Z^1$, $Z^2$, and $Z^3$ all represent —O—, —CO—O—, or a single bond. Sp$^1$, Sp$^2$, and Sp$^3$ preferably each represent a single bond or an alkylene group having 1 to 10 carbon atoms, preferably each represent a single bond or an alkylene group having 1 to 8 carbon atoms, and more preferably each represent a single bond or an alkylene group having 1 to 4 carbon atoms. The alkylene group is preferably unsubstituted or have one or two or more —CH$_2$— each independently substituted with —O—, —CO—, —CO—O—, or —O—CO—, present in the alkylene group; and more preferably the alkylene group is unsubstituted. Specifically, an unsubstituted alkylene group having 1 to 4 carbon atoms or a single bond is particularly preferable.

Moreover, -Sp$^1$-Z$^1$—, -Sp$^2$-Z$^2$—, and -Sp$^3$-Z$^3$— preferably each independently represent —CO—O—, —CH$_2$—CO—O—, —CH$_2$—CH$_2$—CO—O—, —CH$_2$—CH$_2$—CH$_2$—CO—O—, —CH$_2$—O—, —CH$_2$—CH$_2$—O—, —CH$_2$—CH$_2$—CH$_2$—O—, —CH$_2$—O—CO—O—, —CH$_2$—CH$_2$—O—CO—O—, or —CH$_2$—CH$_2$—CH$_2$—O—CO—O—, and more preferably each independently represent —CO—O—, —CH$_2$—CO—O—, or —CH$_2$—CH$_2$—CO—O—.

A preferably has the following structure:

[Chem. 4]

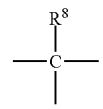

(In the formula, $R^8$ represents a hydrogen atom, —OH, or an alkyl group having 1 to 10 carbon atoms, and one or two or more —CH$_2$— present in the alkyl group may each independently be substituted with —O—, —S—, —CH=CH—, —C≡C—, —CO—O—, or —O—CO—.) This is to enhance the solubility in the liquid crystal composition and storage stability. Here, from the viewpoints of ease of production and ready availability of raw materials, $R^8$ preferably represents a hydrogen atom, —OH, an alkyl group having 2 to 10 carbon atoms, or —O—CO—R$^9$ (R$^9$ represents an alkyl group having 1 to 9 carbon atoms), and particularly preferably represents a hydrogen atom.

The compound represented by general formula (I) of the present invention is preferably a compound represented by general formula (I-a).

[Chem. 5]

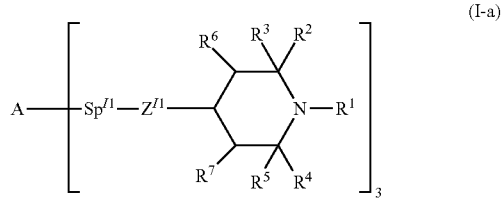

(I-a)

(In the formula, $R^1$, $R^2$, $R^3$, $R^4$, $R^5$, $R^6$ and $R^7$ are each independently the same as $R^1$, $R^2$, $R^3$, $R^4$, $R^5$, $R^6$, and $R^7$ in general formula (I), A is the same as A in general formula (I-M), $Z^{I1}$ represents —O—, —S—, —CO—, —CO—O—, —O—CO—, —NH—, or a single bond, Sp$^{I1}$ represents a single bond or an alkylene group having 1 to 10 carbon atoms, and $R^1$, $R^2$, $R^3$, $R^4$, $R^5$, $R^6$, $R^7$, $Z^{I1}$, and Sp$^{I1}$ that are each present in a plurality may be the same or different from one another.)

$Z^{I1}$ preferably represents —O—, —CO—O—, or a single bond. Sp$^{I1}$ preferably represents a single bond or an unsubstituted alkyl group having 1 to 4 carbon atoms, and is preferably linear.

The compound represented by general formula (I) or general formula (I-a) is preferably a compound represented by general formula (I-b).

[Chem. 6]

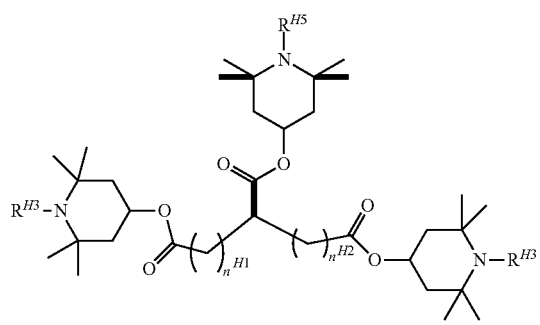

(I-b)

(In the formula, $R^{H3}$, $R^{H4}$, and $R^{H5}$ are each independently the same as $R^1$ in general formula (I), and $n^{H1}$ and $n^{H2}$ each independently represent an integer of 0 to 4.)

In general formula (I-b), $R^{H3}$, $R^{H4}$, and $R^{H5}$ particularly preferably each represent a hydrogen atom. In the case of the alkyl group, the number of carbon atoms is preferably 1 to 8, preferably 1 to 5, preferably 1 to 3, and more preferably 1.

Preferable specific examples of the compound represented by general formula (I) of the present invention are described below, but the present invention is not limited to these examples.

Among compounds represented by general formula (I), compounds represented by general formulae (I-1) to (I-14) are particularly preferable.

[Chem. 7]

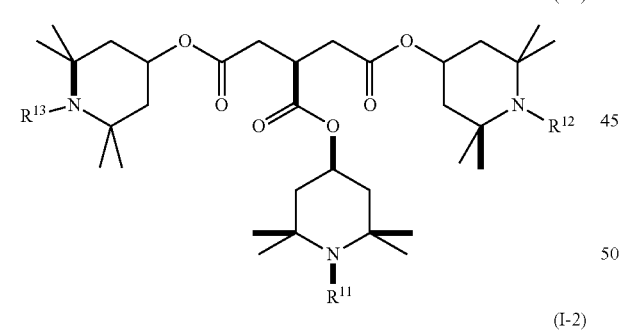

(I-1)

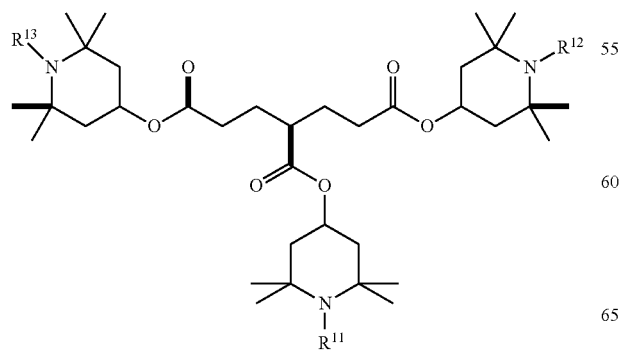

(I-2)

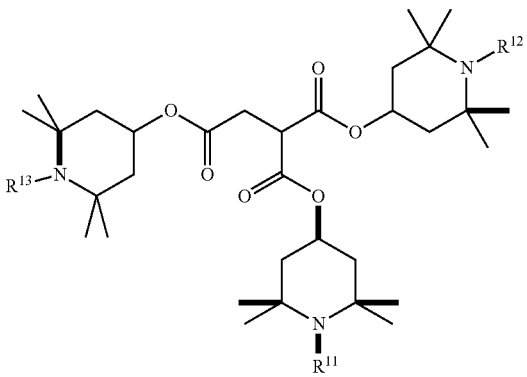

(I-3)

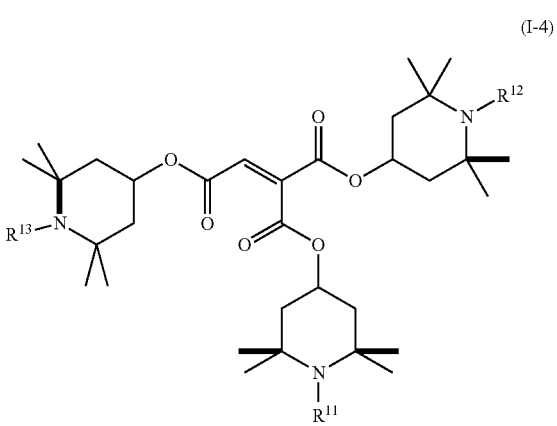

(I-4)

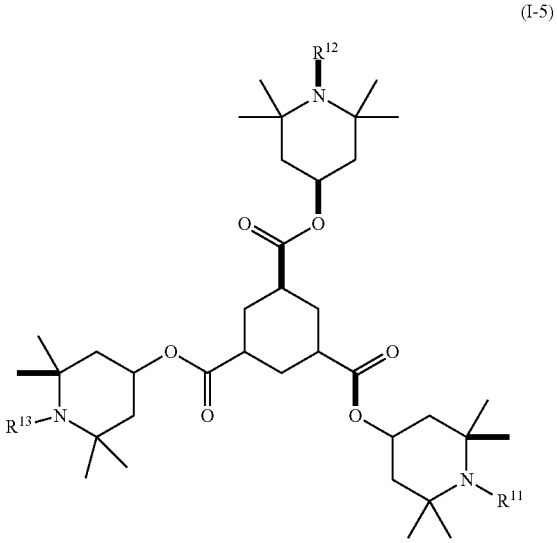

(I-5)

(I-6)
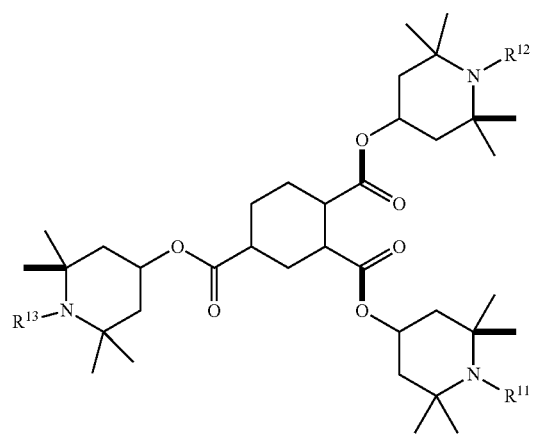
(I-10)
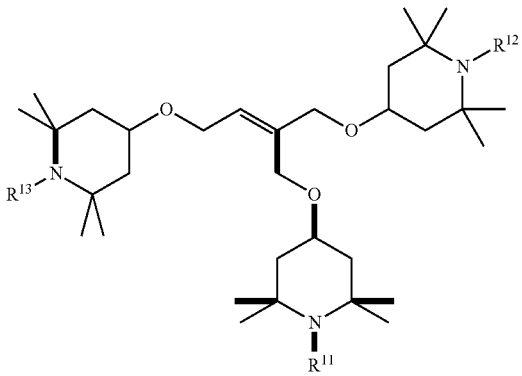
[Chem. 8]
(I-7)
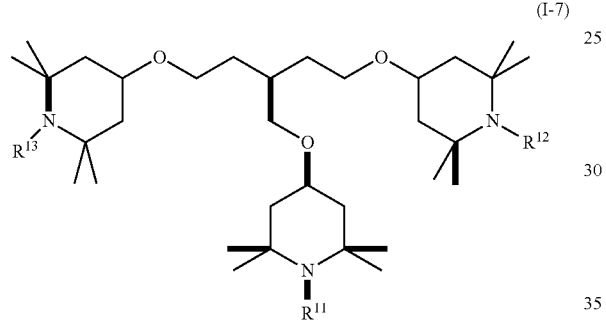
(I-11)
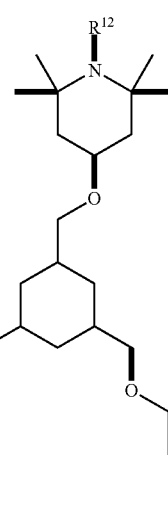
(I-8)
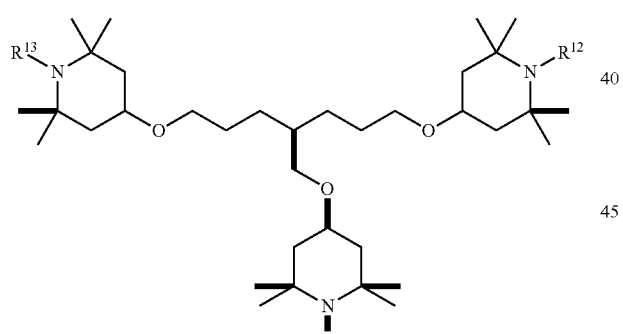
(I-9)
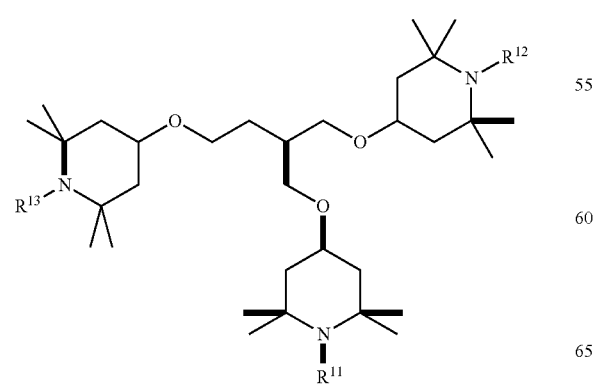
(I-12)
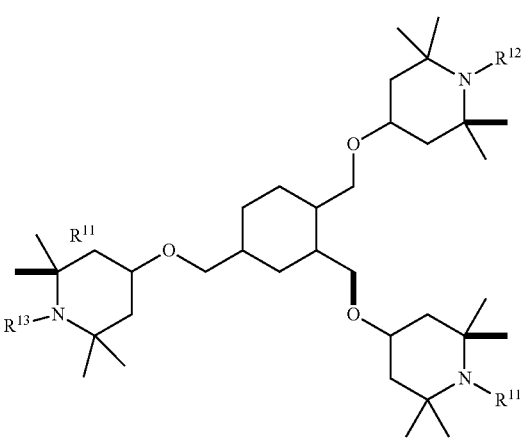

-continued (I-13)

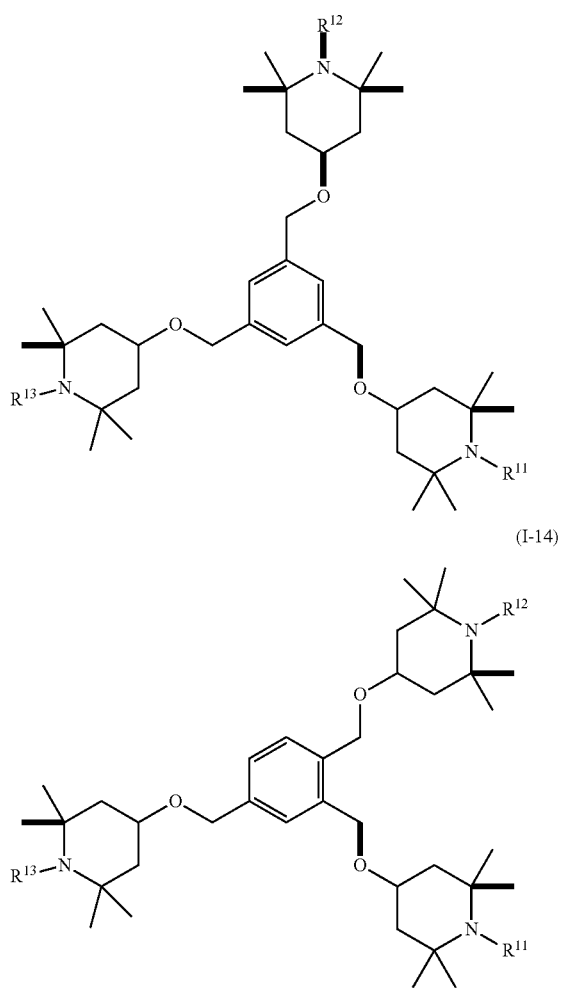

(I-14)

(In the formulae, $R^{11}$, $R^{12}$, and $R^{13}$ are each independently the same as $R^1$ in general formula (I).)

Note that two or more adjacent —$CH_2$— in general formula (I) are never each independently substituted with —O—, —S—, —CO—O—, —O—CO—, —OCF$_2$—, or —CF$_2$O—.

In the present invention, the compounds represented by general formulae (I-1) to (I-14) can be produced as follows. Naturally, the gist and application range of the present invention are not limited by these production examples.

(Method 1) Method for Synthesizing Compound Represented by General Formula (I-1)

[Chem. 9]

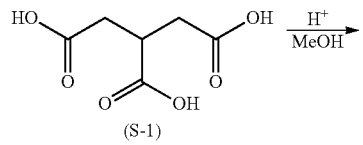

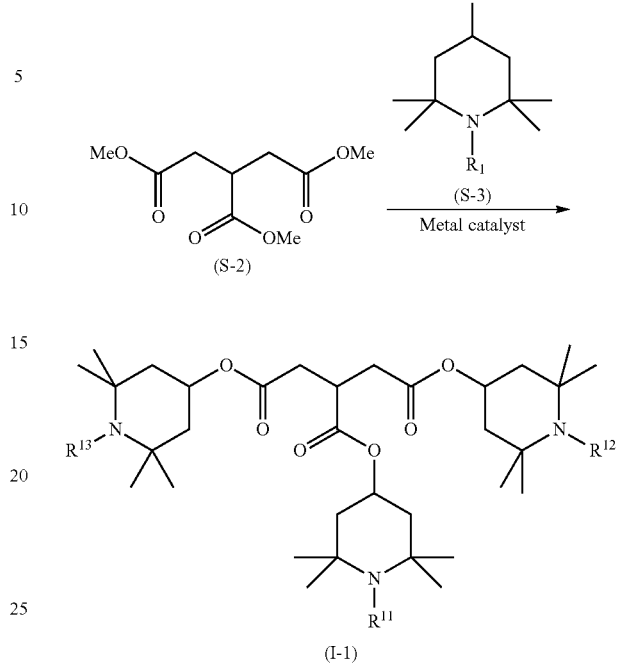

A trimethyl ester (S-2) can be obtained by reacting tricarboxylic acid (S-1) with methanol in the presence of an acid catalyst.

The solvent used may be any solvent with which the reaction smoothly proceeds, and an aromatic solvent, such as toluene, benzene, or xylene, or methanol itself is preferably used as the solvent. The aromatic solvent is preferably benzene or toluene, and these solvents may be used alone or in combination as a mixture as needed. The reaction temperature may be any temperature at which the reaction proceeds smoothly, and is preferably from room temperature to a temperature at which the reaction solvent refluxes.

The acid catalyst used may be any acid catalyst with which the reaction smoothly proceeds, and is preferably p-toluenesulfonic acid, chlorotrimethylsilane, sulfuric acid, or the like, and is more preferably p-toluenesulfonic acid or sulfuric acid.

Next, the trimethyl ester (S-2) and tetramethylpiperidinol (S-3) are reacted to obtain a compound represented by general formula (I-1). An example of the reaction is a method that involves heating (S-2) and (S-3) in the presence of a metal catalyst and removing generated methanol. Examples of the metal catalyst include Al(III), Ti(IV), Sb(III), Sn(IV), Zn(II), and La(III).

The solvent used may be any solvent with which the reaction smoothly proceeds, and is preferably an aromatic solvent, such as toluene, benzene, xylene, or mesitylene, or an ether solvent such as diisopropyl ether, and more preferably toluene or xylene, which has a high boiling point, in order to increase the reaction temperature. These solvents may be used alone or in combination as a mixture as needed.

The reaction temperature may be any temperature at which the reaction proceeds smoothly, is preferably from room temperature to a temperature at which the reaction solvent refluxes, and is more preferably from 40° C. to the temperature at which the solvent refluxes.

(Method 2) Method for Synthesizing Compound Represented by General Formula (I-1)

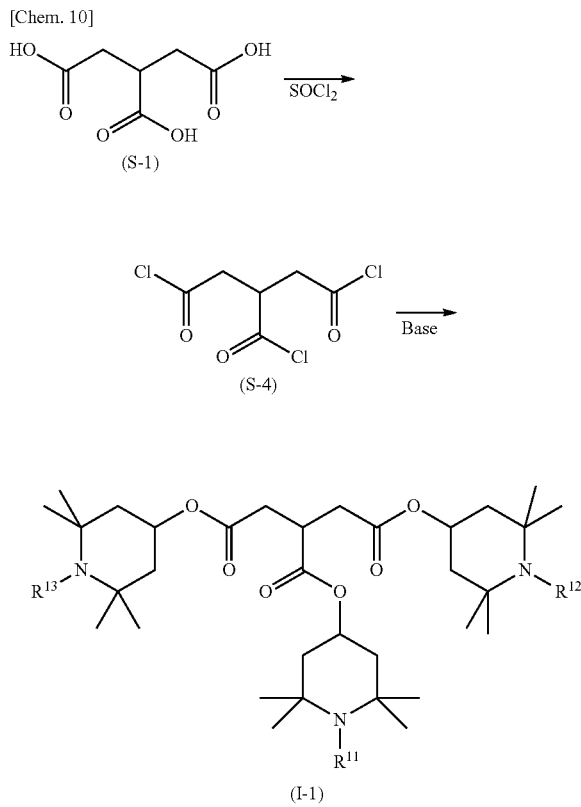

(Method 3) Method for Synthesizing Compound Represented by General Formula (I-13)

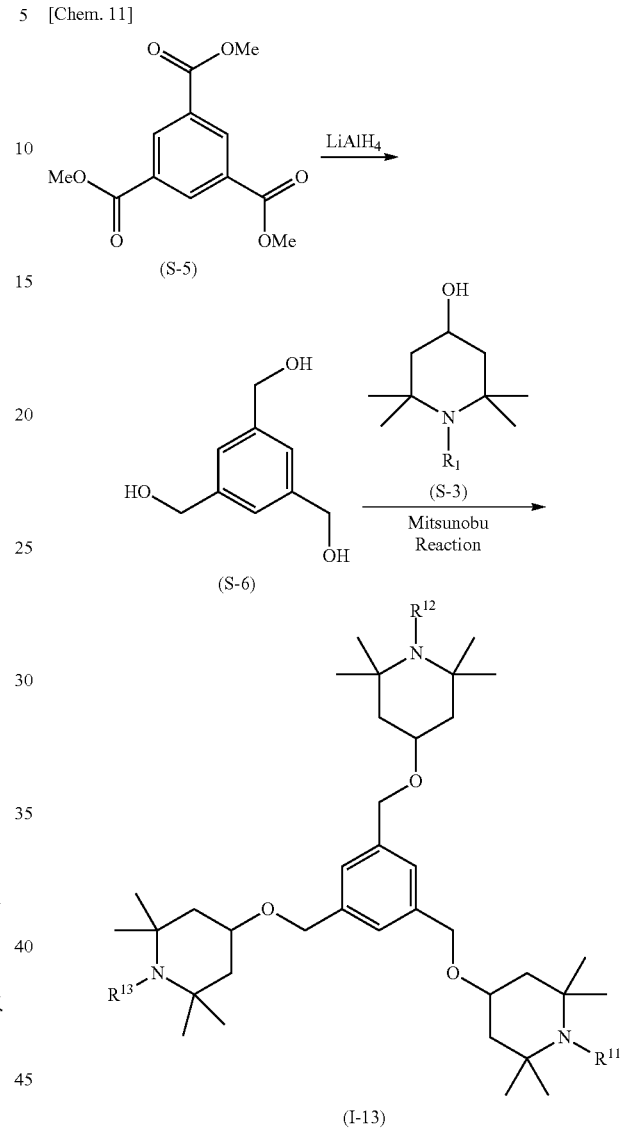

An acid chloride (S-4) can be obtained by reacting tricarboxylic acid (S-1) with thionyl chloride or oxalic acid chloride.

The solvent used may be any solvent with which the reaction smoothly proceeds, and a chlorine solvent or an aromatic solvent is preferably used. Preferable examples of the chlorine solvent include dichloromethane, chloroform, and 1,2-dichloroethane, and preferable examples of the aromatic solvent include benzene and toluene.

The reaction temperature may be any temperature at which the reaction proceeds smoothly, and is preferably from room temperature to a temperature at which the reaction solvent refluxes.

Next, tetramethylpiperidinol (S-4) is reacted in the presence of a base to obtain a compound represented by general formula (I-1). Examples of the base include organic bases, for example, pyridine, triethylamine, N,N-dimethylaminopyridine, and diisopropylethylamine.

The solvent used may be any solvent with which the reaction smoothly proceeds, and a chlorine solvent or an aromatic solvent is preferably used. Preferable examples of the chlorine solvent include dichloromethane, chloroform, and 1,2-dichloroethane, and preferable examples of the aromatic solvent include benzene and toluene.

The reaction temperature may be any temperature at which the reaction proceeds smoothly, and is preferably from room temperature to a temperature at which the reaction solvent refluxes.

A triol (S-6) can be obtained by reacting trimethyl ester (S-5) with an appropriate reducing reagent, for example, lithium aluminum hydride (LiAlH$_4$).

The solvent used may be any solvent with which the reaction smoothly proceeds, and an ether solvent is preferably used. Preferable examples of the ether solvent include diethyl ether and tetrahydrofuran.

The reaction temperature may be any temperature at which the reaction proceeds smoothly, and is preferably from room temperature to a temperature at which the reaction solvent refluxes.

Next, the triol (S-6) and tetramethylpiperidinol (S-3) are subjected to a Mitsunobu reaction to obtain a compound represented by general formula (I-13). An example of the reactant used in the Mitsunobu reaction is a combination of triphenylphosphine and azodicarboxylic acid diethyl ester.

The solvent used may be any solvent with which the reaction smoothly proceeds, and an ether solvent is preferably used. Preferable examples of the ether solvent include diethyl ether and tetrahydrofuran. The reaction temperature may be any temperature at which the reaction proceeds smoothly, and is preferably room temperature.

(Method 4) Method for Synthesizing Compound Represented by General Formula (I-13)

[Chem. 12]

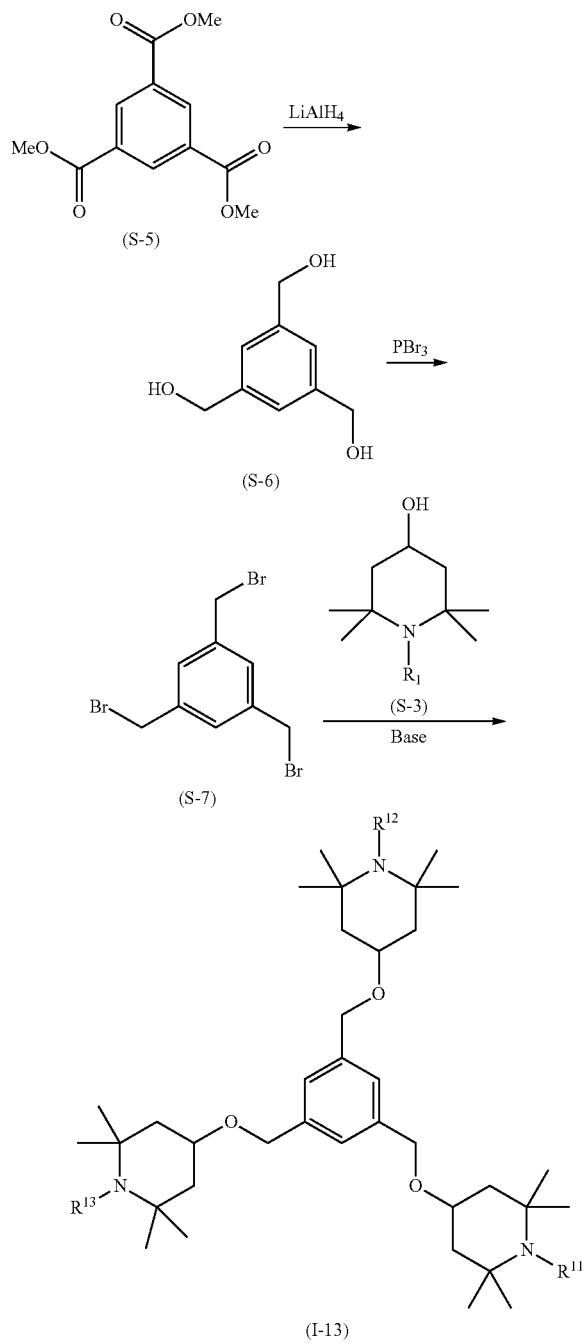

(I-13)

The triol (S-6) obtained in the method 3 is brominated to obtain tribromide (S-7). Phosphorus tribromide, hydrogen bromide, etc., can be used as the brominating agent. The solvent used may be any solvent with which the reaction smoothly proceeds, and a halogen solvent or acetic acid is preferably used. Preferable examples of the halogen solvent include dichloromethane and 1,2-dichloroethane. The reaction temperature may be any temperature at which the reaction proceeds smoothly, and is preferably from room temperature to a temperature at which the reaction solvent refluxes.

Next, tetramethylpiperidinol (S-3) may be reacted in the presence of a base to obtain a compound represented by general formula (I-13). Examples of the base include hydrogenated sodium, sodium methoxide, sodium ethoxide, and potassium t-butoxide.

The solvent used may be any solvent with which the reaction smoothly proceeds, and an ether solvent, a polar solvent, etc., are preferably used. Preferable examples of the ether solvent include 1,4-dioxane, 1,3-dioxane, tetrahydrofuran, diethyl ether, and t-butyl methyl ether; and preferable examples of the polar solvent include N,N-dimethylformamide, N, N-dimethylacetamide, N-methylpyrrolidone, dimethyl sulfoxide, sulfolane, methanol, and ethanol.

The reaction temperature may be any temperature at which the reaction proceeds smoothly, and is preferably from room temperature to a temperature at which the reaction solvent refluxes.

In the steps of the methods 1 to 4 described above, the compound (I) can be purified as needed. Examples of the purification method include chromatography, recrystallization, reprecipitation, and adsorption. Specific examples of the purifier used in chromatography include silica gel, $NH_2$ silica gel, alumina, and activated carbon. Examples of the solvent used in this process include hexane, toluene, and ethyl acetate. Examples of the solvent used in recrystallization or reprecipitation include hexane, toluene, acetone, ethyl acetate, and ethanol. These solvents may be used alone or in combination as a mixture as needed. An example of the purifier used in adsorption is activated carbon. Examples of the solvent used in this process include hexane, toluene, acetone, and ethyl acetate.

EXAMPLES

The present invention will now be described in further detail through examples, which do not limit the present invention. In the description below, "%" used for compositions of examples and comparative examples means "% by mass". The purity of the compound was analyzed by gas chromatography.

(Example 1) Production of Compound (I-1-a)

[Chem. 13]

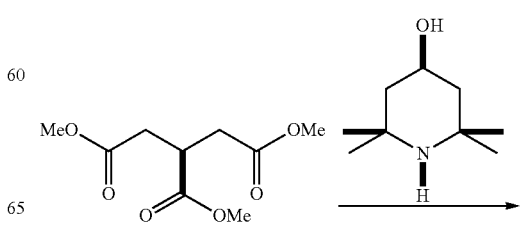

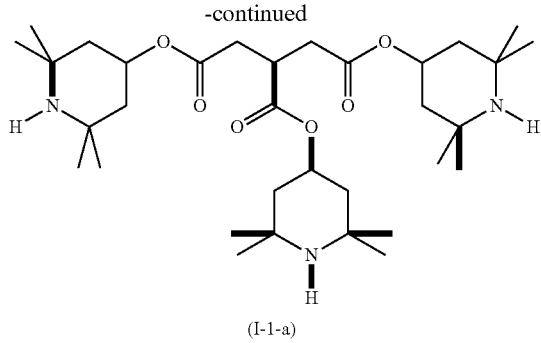

(I-1-a)

In a reactor equipped with a stirrer, a thermometer, a condensing tube, and a Dean-Stark trap, 4-hydroxy-2,2,6,6-tetramethylpiperidine (4.32 g), 1,2,3-propanetricarboxylic acid trimethyl ester (2.00 g), and dibutyl tin oxide (0.28 g) were dissolved in xylene (28 mL), and the resulting solution was refluxed under heating for 48 hours in a nitrogen atmosphere. During the course, generated methanol was removed by molecular sieves. The resulting product was cooled to room temperature and then washed by adding water. The resulting product was purified by recrystallization, and (I-1-a) was obtained as colorless powder. The yield was 1.12 g. The melting point was 110° C.

$^1$H-NMR (400 MHz, CDCl$_3$): 1.05-1.16 (m, 24H), 1.21 (s, 18H), 1.87-1.92 (m, 6H), 2.54 (dd, J=6.2 Hz, 16.6 Hz, 2H), 2.70 (dd, J=7.1 Hz, 16.6 Hz, 2H), 3.16-3.23 (m, 1H), 5.13-5.23 (m, 3H).

GC-MS (EI): m/z 594 [M+H$^+$], 578 [M−15$^+$]

(Example 2) Production of Compound (I-2-a)

[Chem. 14]

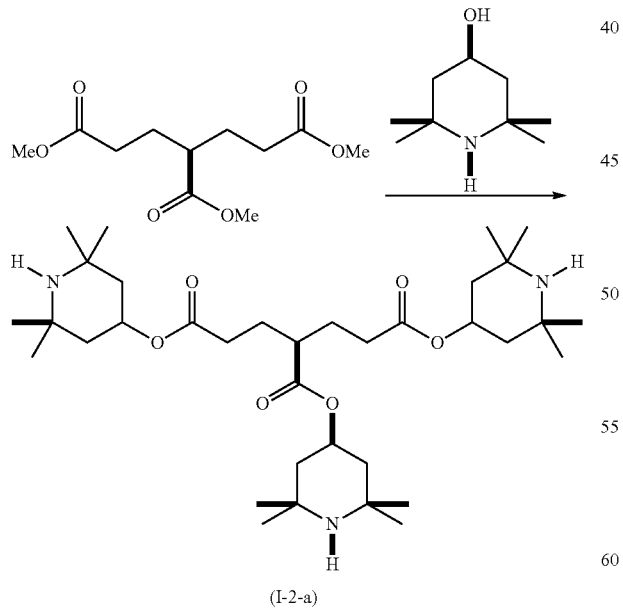

(I-2-a)

In a reactor equipped with a stirrer, a thermometer, a condensing tube, and a Dean-Stark trap, 4-hydroxy-2,2,6,6-tetramethylpiperidine (4.32 g), 1,3,5-pentanetricarboxylic acid trimethyl ester (2.26 g), and dibutyl tin oxide (0.28 g) were dissolved in xylene (28 mL), and the resulting solution was refluxed under heating for 24 hours in a nitrogen atmosphere. During the course, generated methanol was removed by molecular sieves. The resulting solution was cooled to room temperature and then washed by adding water. The resulting product was purified by recrystallization, and (I-2-a) was obtained as colorless powder. The yield was 1.50 g.

GC-MS (EI): m/z 622 [M+H$^+$], 606 [M−15$^+$]

(Example 3) Production of Compound (I-3-a)

[Chem. 15]

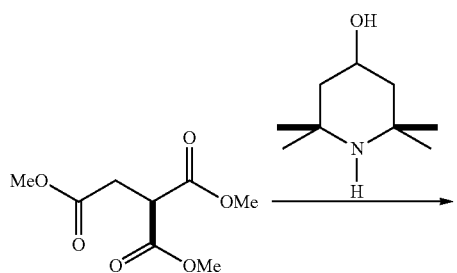

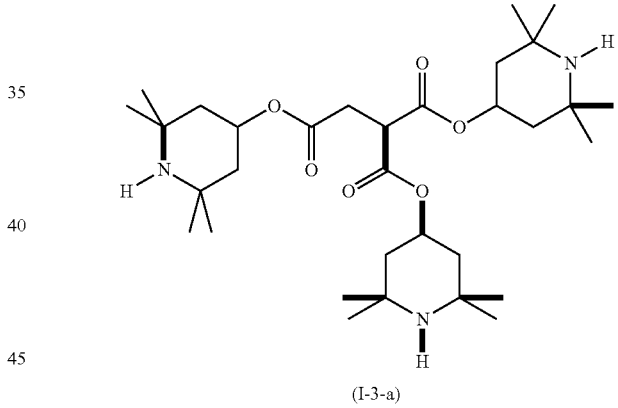

(I-3-a)

In a reactor equipped with a stirrer, a thermometer, a condensing tube, and a Dean-Stark trap, 4-hydroxy-2,2,6,6-tetramethylpiperidine (4.32 g), 1,1,2-ethanetricarboxylic acid trimethyl ester (1.88 g), and dibutyl tin oxide (0.28 g) were dissolved in xylene (28 mL), and the resulting solution was refluxed under heating for 48 hours in a nitrogen atmosphere. During the course, generated methanol was removed by molecular sieves. The resulting product was cooled to room temperature and then washed by adding water. The resulting product was purified by silica gel chromatography, and (I-3-a) was obtained as a pale yellow viscous liquid. The yield was 4.80 g.

GC-MS (EI): m/z 580 [M+H$^+$], 564 [M−15$^+$]

(Example 4) Production of Compound (I-5-a)

[Chem. 16]

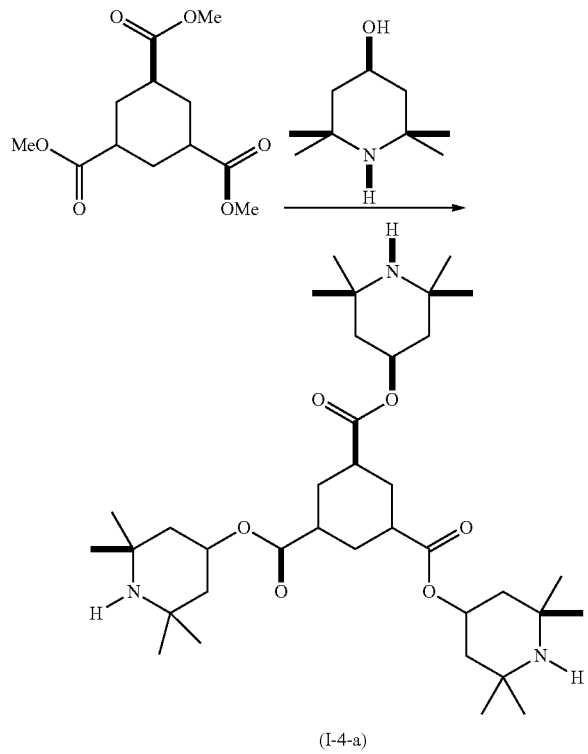

(I-4-a)

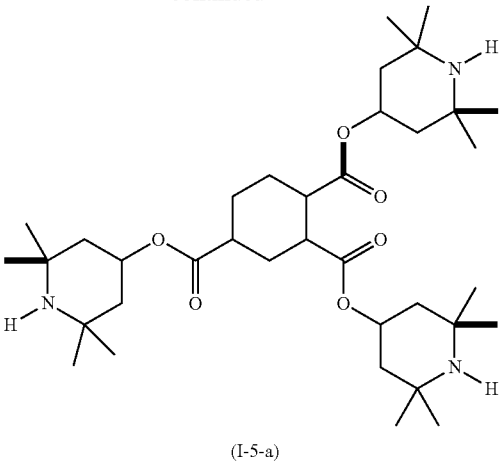

(I-5-a)

In a reactor equipped with a stirrer, a thermometer, a condensing tube, and a Dean-Stark trap, 4-hydroxy-2,2,6,6-tetramethylpiperidine (4.32 g), 1,3,5-cyclohexanetricarboxylic acid trimethyl ester (2.37 g), and dibutyl tin oxide (0.28 g) were dissolved in xylene (28 mL), and the resulting solution was refluxed under heating for 48 hours in a nitrogen atmosphere. During the course, generated methanol was removed by molecular sieves. The resulting product was cooled to room temperature and then washed by adding water. The resulting product was purified by silica gel chromatography, and (I-4-a) was obtained as a pale yellow liquid. The yield was 5.24 g.

GC-MS (EI): m/z 634 [M+H$^+$], 618 [M−15$^+$]

(Example 5) Production of Compound (I-6-a)

[Chem. 17]

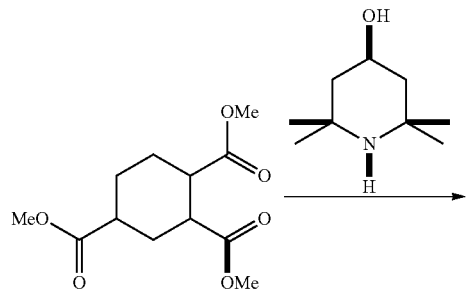

In a reactor equipped with a stirrer, a thermometer, a condensing tube, and a Dean-Stark trap, 4-hydroxy-2,2,6,6-tetramethylpiperidine (4.32 g), 1,2,4-cyclohexanetricarboxylic acid trimethyl ester (2.37 g), and dibutyl tin oxide (0.28 g) were dissolved in xylene (28 mL), and the resulting solution was refluxed under heating for 48 hours in a nitrogen atmosphere. During the course, generated methanol was removed by molecular sieves. The resulting product was cooled to room temperature and then washed by adding water. The resulting product was purified by silica gel chromatography, and (I-5-a) was obtained as a pale yellow liquid. The yield was 5.35 g.

GC-MS (EI): m/z 634 [M+H$^+$], 618 [M−15$^+$]

(Examples 6 to 10) Preparation of Liquid Crystal Composition

A liquid crystal composition (H) having the following composition was prepared.

[Chem. 18]

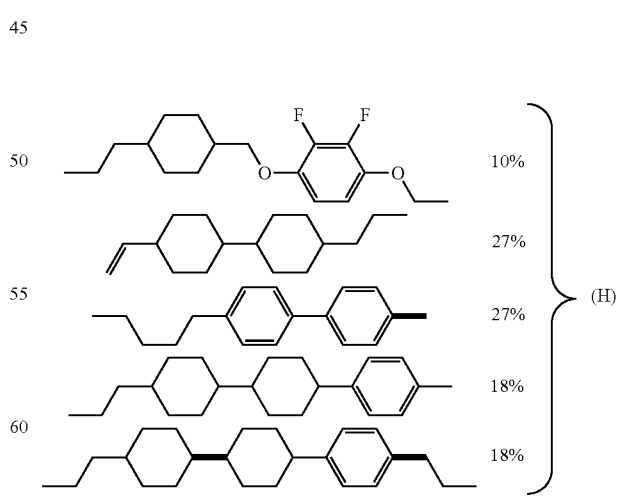

To this mother liquid crystal (H), 500 ppm of compounds (I-1-a) to (I-5-a) obtained in Examples 1 to 5 were added. The properties measured were as follows.

Initial VHR: at 60 Hz frequency, 1 V application voltage, the voltage holding ratio (%) at 333 K was evaluated in three grades.

A: 98 to 100%
B: 95 to 98%
C: 95% or less

VHR under UV exposure: The liquid crystal composition was irradiated with 180 J/m² UV light from an ultrahigh pressure mercury lamp through a 0.5 mm-thick glass while the temperature was maintained at 20° C. (irradiation intensity was 0.1 W/m², 30 minutes, at 366 nm). The voltage holding ratio of the liquid crystal after the UV irradiation was measured as in the VHR measurement described above. Evaluation was conducted in the following three grades.

A: 90 to 100%
B: 75 to 90%
C: 75% or less

Solubility: To the liquid crystal composition, 500 ppm of the subject compound was added, and the resulting mixture was stirred to homogeneity under heating at 100° C. The resulting solution was cooled to 25° C. and left to stand one day, and the state of dissolution was evaluated with naked eye in three grades.

A: The compound was completely dissolved.
B: The compound remained slightly undissolved and separated.
C: The compound remained partly undissolved and separated.

Comparative Example 1

In a comparative example, the properties were measured without further adding a stabilizer compound to the mother liquid crystal (H).

Comparative Example 2

To the mother liquid crystal (H), a compound (R-1) having a similar hindered amine skeleton was added in an amount of 500 ppm, and the properties were measured.

[Chem. 19]

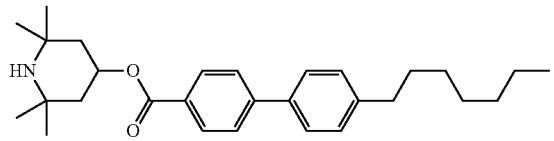

(R-1)

The results of the measurements are indicated below.

TABLE 1

| Example | Compound added | Amount added | Initial VHR | VHR under UV exposure | Solubility |
|---|---|---|---|---|---|
| Example 6 | I-1-a | 500 ppm | A | A | A |
| Example 7 | I-2-a | 500 ppm | A | A | A |
| Example 8 | I-3-a | 500 ppm | A | A | A |
| Example 9 | I-4-a | 500 ppm | A | A | A |
| Example 10 | I-5-a | 500 ppm | A | A | A |

TABLE 1-continued

| Example | Compound added | Amount added | Initial VHR | VHR under UV exposure | Solubility |
|---|---|---|---|---|---|
| Comparative Example 1 | None | 500 ppm | A | B | — |
| Comparative Example 2 | R-1 | 500 ppm | A | A | C |

When Examples 6 to 10 and Comparative Example 1 are compared, it is clear that adding the compound of the present invention improves the light-resisting VHR. When Examples 6 to 10 and Comparative Example 2 were compared, it is clear that the compound of the present invention has excellent solubility in the liquid crystal composition. These results show that the compound of the invention of the present application has high solubility in the liquid crystal composition and has an effect of preventing degradation of the liquid crystal composition.

The invention claimed is:

1. A compound represented by the formula (I-b)

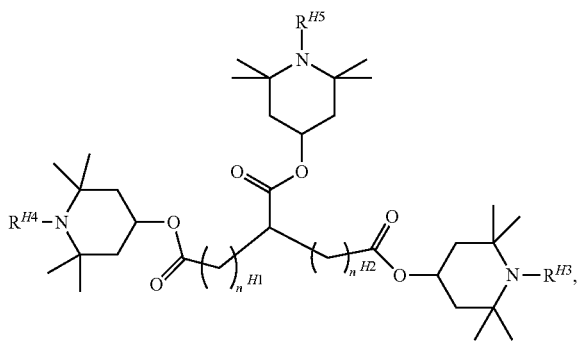

(I-b)

wherein in the formula, $R^{H3}$, $R^{H4}$, and $R^{H5}$ are each independently a hydrogen atom, and $n^{H1}$ and $n^{H2}$ each independently represent an integer of 1 to 4.

2. A composition comprising one or two or more of the compounds according to claim 1.

3. The composition according to claim 2, wherein the composition exhibits a liquid crystal phase at room temperature.

4. A liquid crystal display device, comprising the composition according to claim 2.

5. The compound according to claim 1, wherein the compound is represented by the formula (I-1) or (I-2),

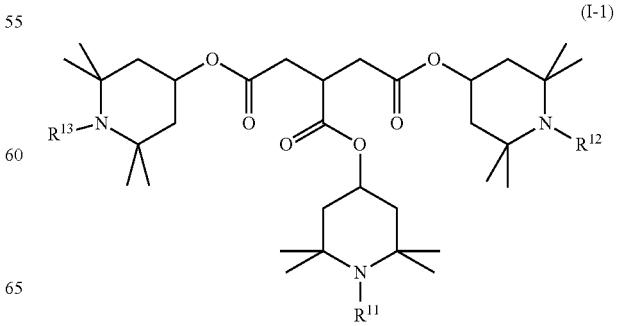

(I-1)

-continued
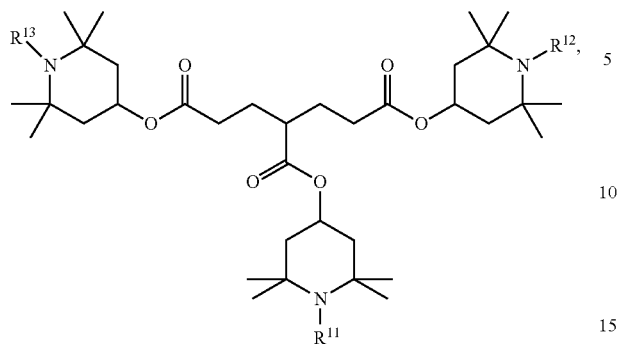
(I-2)
$R^{11}$, $R^{12}$, and $R^{13}$ are each independently a hydrogen atom.
6. The composition according to claim 3, wherein the compound can be dissolved completely at 500 ppm into the composition.
* * * * *